United States Patent [19]
Chen

[11] Patent Number: 6,150,623
[45] Date of Patent: Nov. 21, 2000

[54] BACK-FLIP MEDICAL FOOTPEDAL

[75] Inventor: Jerry S. J. Chen, Orange, Calif.

[73] Assignee: Allergan, Irvine, Calif.

[21] Appl. No.: 09/140,874

[22] Filed: Aug. 27, 1998

[51] Int. Cl.⁷ .............................. H01H 3/14; G05G 1/14; G05G 9/02
[52] U.S. Cl. .............................. 200/86.5; 74/478; 74/512
[58] Field of Search .............................. 200/86.5, 61.89; 74/512, 560, 561, 562, 563, 478, 478.5

[56] References Cited

U.S. PATENT DOCUMENTS

| | | | |
|---|---|---|---|
| 4,168,707 | 9/1979 | Douvas et al. | 128/276 |
| 4,354,071 | 10/1982 | Pietschmann | 200/86.5 |
| 4,933,843 | 6/1990 | Scheller et al. | 364/413.01 |
| 4,983,901 | 1/1991 | Lehmer | 318/685 |
| 5,091,656 | 2/1992 | Gahn | 307/119 |
| 5,268,624 | 12/1993 | Zanger | 318/551 |
| 5,983,749 | 11/1999 | Holtorf | 74/560 |

FOREIGN PATENT DOCUMENTS 0085518  8/1983  European Pat. Off. .
WO9302627 2/1993 WIPO .

*Primary Examiner*—J. R. Scott
*Attorney, Agent, or Firm*—Walter A. Hackler

[57] ABSTRACT

A footpedal suitable for use as an accelerator type pedal or a toe activated pedal includes a frame having a heel portion and a toe portion with the heel and toe portions being disposed at an angle with one another. A wedge having a generally triangular cross section is provided with first and second sides subtending a front of the wedge. A hinge pivotally mounts the wedge to the frame for enabling the wedge to be flipped between a first position having the wedge first side generally aligned with the frame heel portion and extending therefrom and a second position having the wedge second side generally aligned with the frame toe portion and extending therefrom. In each opposition, a substantially planar relationship is established for a user in either the accelerator configuration or toe configuration. A switch lever is mounted on either side of the pedal for actuating a switch by lateral movement of the user's foot. A switch in operative engagement with the wedge reverses a functional role of the foot activated switch levers in response to flipping the wedge between first and second positions.

19 Claims, 5 Drawing Sheets

BACK-FLIP MEDICAL FOOTPEDAL

BACKGROUND OF THE INVENTION

The present invention generally relates to footpedals for controlling various apparatus and is more particularly directed to a foot operated control for ophthalmic surgical apparatus such as, for example, for controlling the operation of handpieces during ophthalmic surgery. Still more particularly, the present invention is directed to footpedal apparatus for the control of irrigation, aspiration in connection with phacoemulsification of natural lenses.

Ophthalmic surgical apparatus such as phacoemulsification apparatus, hereinabove noted, typically includes operating controls for regulating perimeters, or functions, of the apparatus. The apparatus generally includes a handpiece for ultrasonic emulsifying a natural lens while irrigating the eye and aspirating particles of emulsified lens.

Various modalities of operation may be utilized in difficult phacoemulsification apparatus which pertain to controlling various phases of the procedure.

Typical apparatus includes a control cabinet, power supply, vacuum pump, as well as associated electronic hardware for operating a multi-function handpiece in order to sonically emulsify eye tissue, irritate the eye with saline solution, and aspirate the emulsified lens from the eye.

The control system typically utilizes a footpedal module which enables the operator to control many perimeters associated with the operation. Such perimeters include the aspiration rate, the intensity power applied to phaco handpiece as well as modes of operation of the handpiece itself. Thus, the use of the handpiece is facilitated by delegating these control functions to the footpedal device.

Heretofore, footpedal device systems have been utilized which provide a variety of pneumatic and electrical actuators to control the ophthalmic surgical apparatus. As an example, the footpedal control systems are described in U.S. Pat. No. 4,983,901 provide for a virtually unlimited number of control variations and modes for operating phacoemulsification apparatus. This patent is incorporated herewith in its entirety in order to provide a teaching of the multitude of operating perimeters which fall in the scope of the present invention.

Because of the importance of the control features provided by footpedals, such devices must be user friendly in order to provide a surgeon the comfort and reliability expected in order not to initiate any disruption of the surgeon's concentration when performing surgery.

As may be expected, different types of footpedals are preferred by various surgeons, with some surgeons preferring an accelerator type pedal in which the sole of the surgeon's foot is utilized for depression, while others desire a pedal operable by the surgeon's toe in order to depress the pedal.

In the past, this has led to the development of a multitude of footpedal devices of diverse configuration in order to provide the comfort and reliability desired by individual surgeons.

Unfortunately, when phacoemulsification apparatus is utilized by a number of physicians, a change in footpedals is often required, which is often inconvenient and may require recalibration of the apparatus. In addition, such alternative footpedals may not be available or offered by a manufacturer.

Accordingly, it is desirable to provide a footpedal which can be utilized by all attending physicians despite their preference for toe or sole activated pedals. The present invention fulfills that need, while at the same time providing a footpedal which is comfortable to use in either a toe or sole depression configuration.

SUMMARY OF THE INVENTION

A footpedal in accordance with the present invention generally includes a frame having a heel portion and a toe portion with the heel and toe portions being disposed at an angle with one another. A wedge is provided which has a generally triangular cross section with the first and second sides thereof subtending a front of the wedge.

A hinge provides a means for pivotally mounting the wedge to the frame which enables the wedge to be flipped between a first position having the wedge first side generally aligned with the frame heel portion and extending therefrom, and a second position having the wedge second side generally aligned with the frame toe portion and extending therefrom.

The structure of the present invention enables the single footpedal to be suitable for physicians desiring an accelerator type, sole contact footpedal, for controlling attached apparatus, and physicians desiring a toe contact footpedal for controlling such apparatus.

More particularly, and importantly, the footpedal may comprise means for enabling the frame heel portion and the wedge first side to assume a flat planar relationship in the wedge first position and for enabling the frame toe portion and the wedge second side to assume a second planar relationship in the wedge second position.

Thus, in either position of the wedge, the foot pedal in accordance with the present invention, allows a comfortable and uniform flat planar area for contacting the sole or toe of a user without discontinuities therein which may prove to be uncomfortable to the user or interfere with the use of the footpedal.

More particularly, the means for enabling the planar relationship includes mating surface contours in both the frame and the wedge. Still more particularly, the mating surface contours may comprise corrugations in the frame and the wedge.

These corrugations may be aligned with the longitudinal axis of the footpedal, or may be aligned with the transverse axis of the footpedal. In either event, the corresponding corrugations mesh, or nest, with one another when the wedge is either in the first or the second position, which enables alignment of the wedge and frame in one of two planes, depending upon the position of the wedge.

In addition, the footpedal in accordance with the present invention may include a foot activated switch lever, which is disposed adjacent the pedal for enabling activation of the foot activated switch lever by lateral displacement of the user's foot. Two such foot activated switch levers may be provided with one on each side of the pedal for enabling activation thereof by lateral displacement of the user's foot to the right or left, while maintaining contact with the foot pedal itself in either the first or second position of the wedge.

In view of the alternative positions of wedge, switch means may be provided which is disposed in an operative relationship with the wedge for reversing a functional role of the foot activated switch levers in response to the wedge being flipped between the first and second positions.

BRIEF DESCRIPTION OF THE DRAWINGS

The advantages and features of the present invention would be better understood by the following description when considered in conjunction with the accompanying drawings, in which.

DETAILED DESCRIPTION

Figure 1:
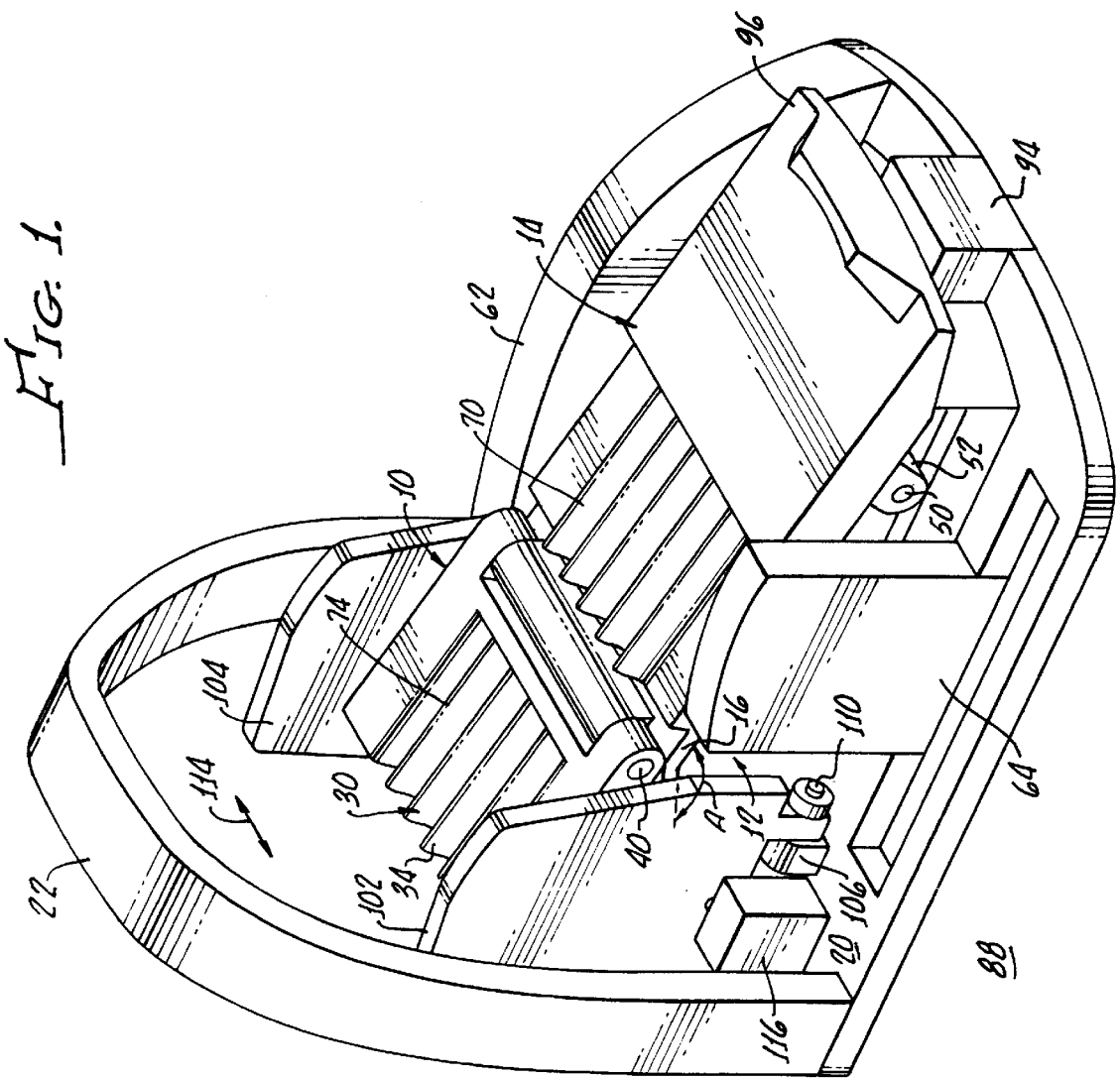
FIG. 1 is a perspective view of the footpedal in accordance with the present invention generally showing frame having a heel portion and a toe portion along with a wedge disposed in a first position in which a wedge first side is generally aligned with a frame heel portion.
Figure 2:
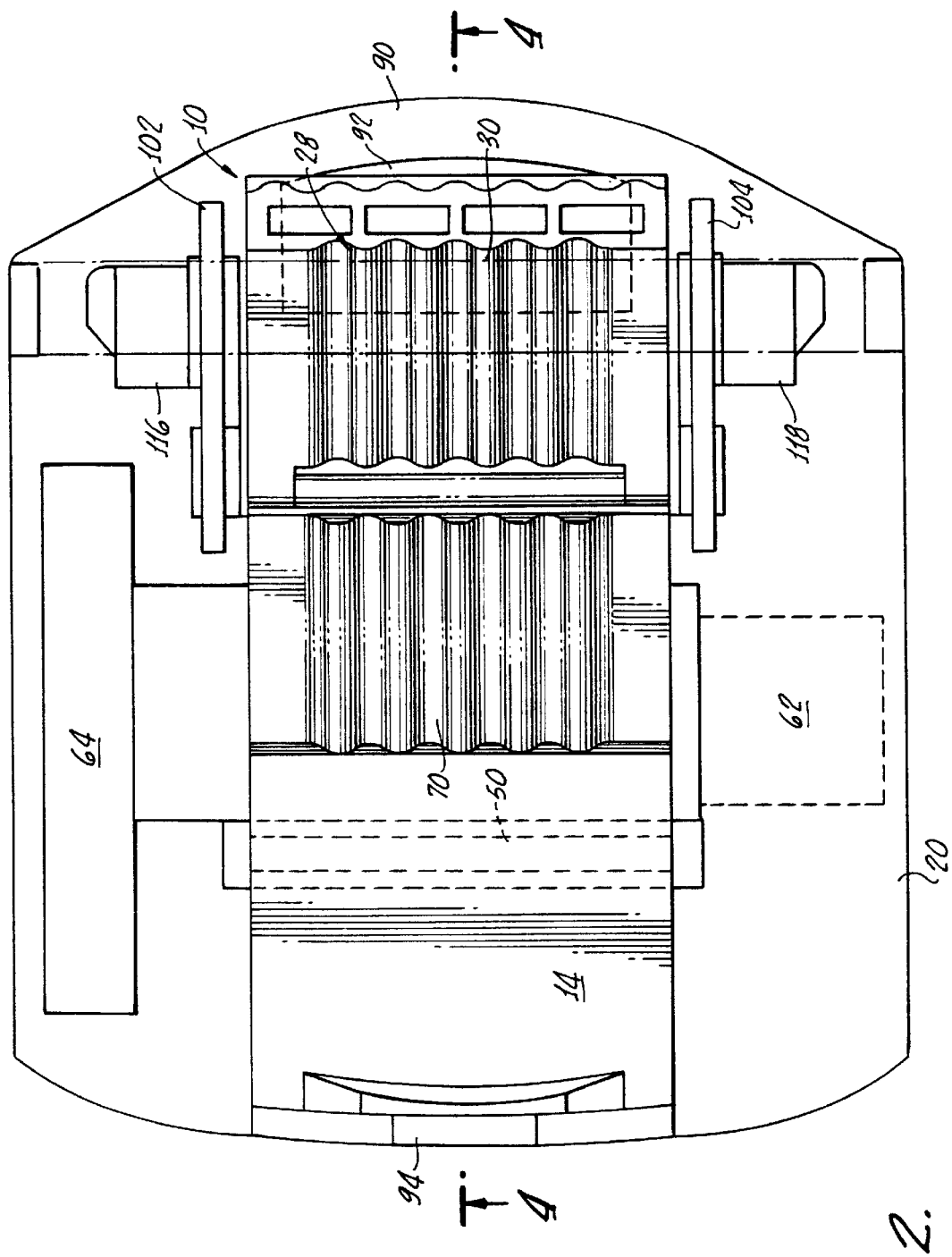
FIG. 2 is a top plane view of the footpedal shown in FIG. 1.

With reference to FIGS. 1 and 2, there is shown a footpedal 10 in accordance with the present invention, which generally includes a frame 12 having a heel portion 14 and a toe portion 16, with the heel portion 14 and the toe portion 16 being disposed at an angle A with one another.

Figure 3:
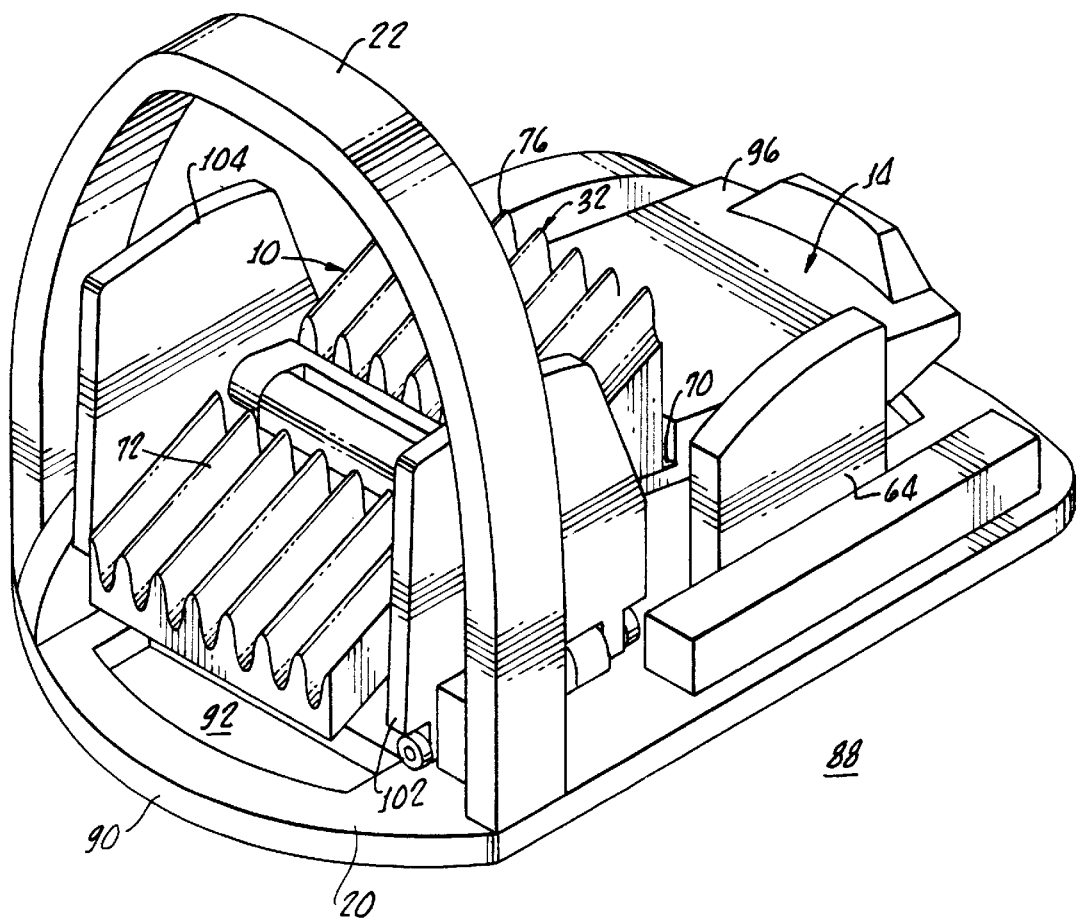
FIG. 3 is a perspective view of the footpedal shown in FIG. 1 with the wedge disposed in a second position and assuming a generally planar relationship with a frame toe portion.

The frame 10 may be formed from any suitable material such as metal or plastic and may be mounted on a base 20 along with a handle 22 for facilitating movement of the footpedal 10 and base as may be necessary to operate the footpedal 10 in either an accelerated type pedal as shown in FIGS. 1 and 2, or in a toe operable configuration as shown in FIG. 3, and hereinafter described in greater detail.

Figure 4:
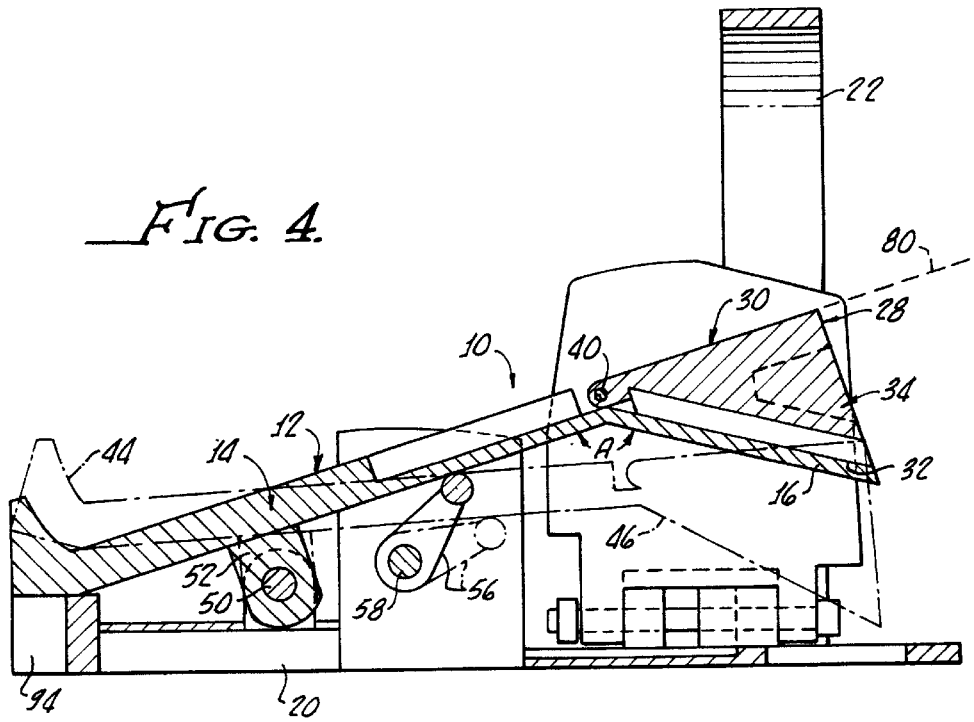
FIG. 4 is a cross sectional view of the footpedal of FIG. 2, showing the wedge in a first position in a flat planar relationship with a frame heel portion.

As also shown in FIG. 4, the footpedal 10 includes a wedge having a generally triangular cross section, with the first side 30 and a second side 32 subtending a front 34 of the wedge 28. The wedge 28 may be formed from any suitable type material such as metal or plastic.

Figure 5:
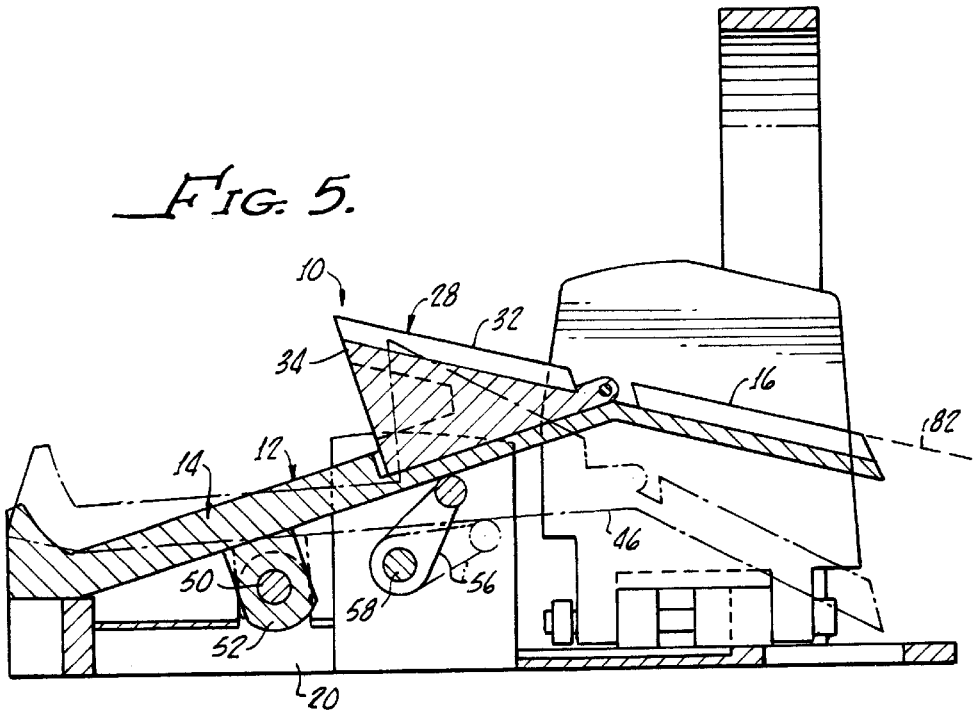
FIG. 5 is a cross sectional view showing the alignment of the wedge and frame toe portion when the wedge is disposed in a second position as hereinafter described in greater detail.
Figure 6:
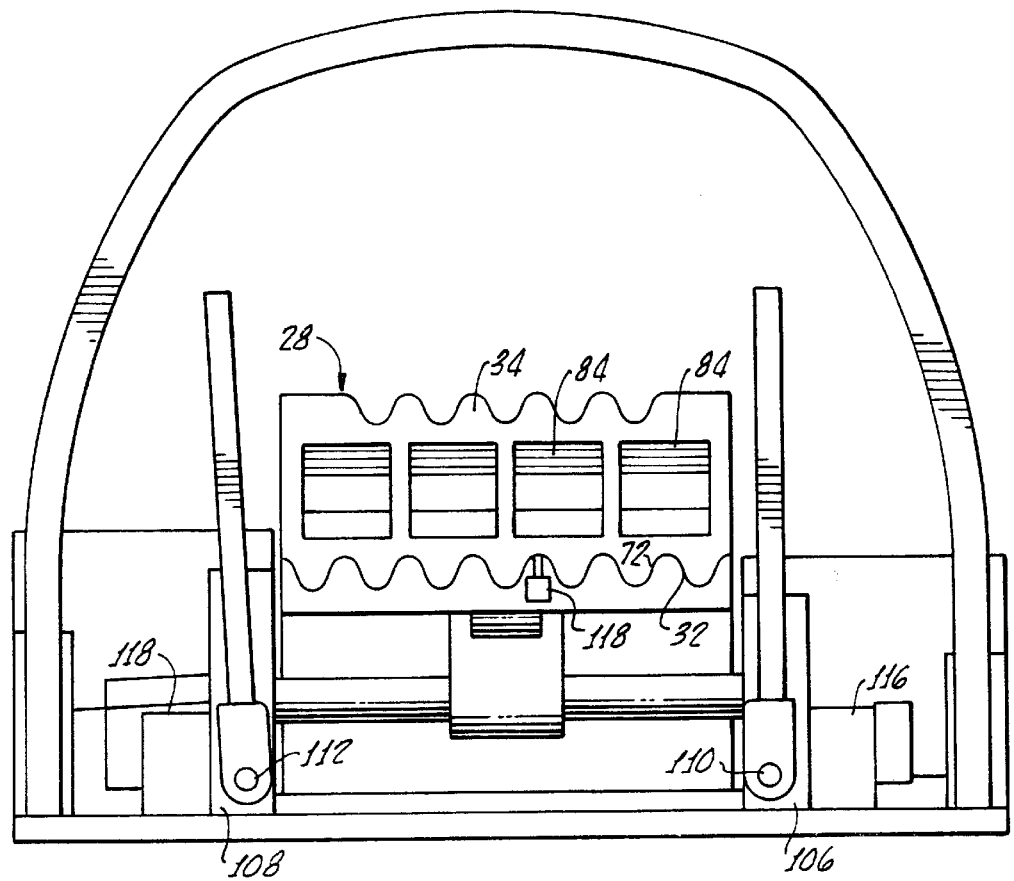
FIG. 6 is a front plane view of the footpedal shown in FIG. 1 showing in greater particularity foot activated levers.

A hinge 40 pivotally mounts the wedge 28 to the frame 12 and provides a means for enabling the wedge 28 to be flipped from a first position as shown in FIGS. 1 and 4, and a second position shown in FIGS. 3 and 5.

In the first position, the wedge first side 30 is generally aligned with the frame heel portion 14 and in the second position, the wedge second side 32 is generally aligned with the frame toe portion 16.

As shown most clearly in FIG. 4 in the first position, the footpedal 10 is operable as an accelerator type foot pedal with a depressed position being shown in broken line 44 and FIG. 4.

As shown in FIG. 5, when the wedge 28 is in the second position, the footpedal 10 is operable as a toe depression pedal with a depressed position being shown in broken line 46 in FIG. 5. In either mode of operation, the footpedal 10 is cause to pivot about a pin 50 (see FIGS. 4, 5) mounting the heel portion 14 of the frame 12 to the base 20 by means of a flange 52.

A restoring force to return the footpedal 10 to original positions after depression, as shown in solid line in FIGS. 4 and 5, is provided by a resilient coupling 56 in a conventional manner. Movement of the pedal about a shaft 58 is provided by a conventional shaft encoder 62 (see FIG. 1) which is connected to an onboard computer control assembly 64 for operating remote apparatus such as, for example, a phacoemulsification device (not shown).

Importantly, mating surface contours, namely, corrugations 70 in the frame heel portion 14, see FIG. 1, and corrugated portions 72 in the frame toe portion 16, see FIG. 3, and corresponding corrugations 74 in the wedge first side 30 and corrugations 76 in the wedge second side 32 provide a means for enabling the frame heel portion 14 to assume a flat planar relationship indicated by the dashed line 80 when the wedge 28 is in the first position and for enabling the frame toe portion 16 and wedge second side 32 to assume a second planar relationship, indicated by the dash line 82 (see FIG. 5) when the wedge 28 is in the second position.

This results in an even support for a user's foot (not shown), which may otherwise be interrupted by a protruding hinge (not shown). Such protrusions may cause not only a comfortable position for the foot, but may interfere with the action of the foot pedal by the user.

It should be appreciated that, while the corrugations 70, 72, 74, 76 are generally aligned with a longitudinal axis of the foot pedal 10, the corrugations may also be transverse to the longitudinal axis. Furthermore, the mating surfaces, while shown as corrugations, may, in fact, assume any mating surface contour to enable the planar relationships hereinabove described.

Further illustrating the mating relationship between the wedge contours 32 and the frame toe portion corrugations 72 is shown in FIG. 4.

Thus, the footpedal 10 in accordance with the present invention can accommodate users preferring an accelerator type arrangement as shown in FIG. 1 or a toe engagement arrangement as shown in FIG. 3 by merely flipping the wedge 28 from the first position as shown in FIG. 1 to the second position as shown in FIG. 3. To facilitate this flipping, a plurality of holes 84 may be provided in a front 34 of the wedge 28 to accommodate a user's finger, or fingers. To reverse the position of the footpedal 10 and base 20 on a floor 88, the handle 22, which also provides a kick guard protection for the footpedal 10, may be used. Alternatively, a second handle, defined by a hole 92 in the base 20, may be utilized for reversing the footpedal 10 position on the floor 88.

A zero switch 94 may be provided and disposed beneath a rear portion of the frame heel portion 14 in order to indicate and provide a signal to the control assembly 64, which is fixed to the frame 20. Electrical interconnections are admitted in the drawings for sake of clarity. The control assembly 64 is configured for cooperating with apparatus (not shown) with which the footpedal 10 is to be used in conjunction therewith.

In that regard, when the footpedal 10 is to be used in conjunction with a phacoemulsification system, for example, foot activated switch levers 102 may be provided. These levers 102 are pivotally attached to the base by brackets 106, 108 and pins 110, 112, which provide means for disposing the foot activated switch levers 102, 104, in a position for lateral displacement, indicated by the arrow 114, of a user's foot (not shown). As a result of such movement, signals to the control assembly 64 are provided by switches 116, 118.

For example, movement of the lever 104 may provide an emergency shut-down of the phacoemulsification equipment with regard to aspiration irrigation fluids, while the lever 102 may be utilized to switch between various modes of operation of the phacoemulsification equipment. All of these functions may be programmed and implemented through the use of the control assembly 64, and/or control equipment associated with the phacoemulsification handpiece. In that regard, a microswitch 118, see FIG. 4, may be disposed in an operative relationship with the wedge 28 for reversing a functional role of the foot activated switch levers 102, 104, in response to the wedge 28 being flipped between the first and second positions.

That is, if an emergency stop situation is to be provided by a right lateral displacement of the foot, as shown in FIG. 4, then the functions of the switch activated levers 102, 104 must be reversed when the wedge 28 is shifted to the second position as shown in FIG. 3.

This is accomplished by utilizing a signal from the microswitch 118 which is interconnected to the control assembly 64 which, when programmed in a conventional manner, can accomplish this objective. Again, interconnecting wires and details with regard to programming are omitted here for the sake of clarity and are obvious to one skilled in the art of programming instrumentation.

Although there has been hereinabove described a specific arrangement of a footpedal in accordance with the present invention for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A footpedal comprising:

a frame having a heel portion and a toe portion, the heel and toe portions being disposed at an angle with one another;

a wedge having a generally triangular cross-section with first and second sides subtending a front of said wedge; and hinge means, pivotally mounting said wedge to said frame, for enabling said wedge to be flipped between a first position, having the wedge first side generally aligned with the frame heel portion and extending therefrom, and a second portion, having the wedge second side generally aligned with the frame toe portion and extending therefrom.

2. The footpedal according to claim 1 further comprising means for enabling the frame heel portion and wedge first side to assume a first planar relationship in the wedge first position and for enabling the frame toe portion and wedge second side to assume a second planar relationship in the wedge second position.

3. The footpedal according to claim 2 wherein the means for enabling the planar relationship comprises mating surface contours in said frame and said wedge.

4. The footpedal according to claim 3 wherein the mating surface contours comprises corrugations in said frame and wedge.

5. The footpedal according to claim 4 wherein the corrugations are aligned with a longitudinal axis of the footpedal.

6. The footpedal according to claim 4 wherein the corrugations are aligned with a transverse axis of the footpedal.

7. The footpedal according to claim 1 further comprising means, defining finger holes in the front of said wedge, for enabling manual flipping of the wedge between the first and second positions.

8. The footpedal according to claim 1 further comprising at least one foot activated switch lever and means disposing the foot activated switch lever adjacent said pedal for enabling activation of the foot activated switch lever by lateral displacement of a user's foot.

9. The foot pedal according to claim 1 further comprising two foot activated switch levers and means disposing one of the foot activated switch levers on each side of said pedal for enabling activation of the foot activated switch levers by lateral displacement of user's foot.

10. The footpedal according to claim 9 further comprising switch means, disposed in an operative relationship with said wedge, for reversing a functional role of the foot activated switch levers in response to the wedge being flipped between the first and second positions.

11. A footpedal comprising:

a frame having a heel portion and a toe portion, the heel and toe portions being disposed at an angle with one another;

a wedge having a generally triangular cross section with first and second sides subtending a front of said wedge;

hinge means, pivotally mounting said wedge to said frame, for enabling said wedge to be flipped between a first position, having the wedge first side generally aligned with the frame heel portion and extending therefrom, and a second portion, having the wedge second side generally aligned with the frame toe portion and extending therefrom; and means, defining corrugations in said frame and wedge, for enabling the frame heel portion and wedge first side to assume a first planar relationship in the wedge first position and for enabling the frame toe portion and wedge second side to assume a second planar relationship in the wedge second position.

12. The footpedal according to claim 11 wherein the corrugations are aligned with a longitudinal axis of the footpedal.

13. The footpedal according to claim 11 wherein the corrugations are aligned with a transverse axis of the footpedal.

14. The footpedal according to claim 11 further comprising means, defining finger holes in the front of said wedge, for enabling manual flipping of the wedge between the front and second positions.

15. The footpedal according to claim 14 further comprising at least one foot activated switch lever and means disposing the foot activated switch lever adjacent said pedal for enabling activation of the foot activated switch lever by lateral displacement of a user's foot.

16. The foot pedal according to claim 14 further comprising two foot activated switch levers and means disposing one of the foot activated switch levers on each side of said pedal, for enabling activation of the foot activated switch levers by lateral displacement of user's foot.

17. The footpedal according to claim 16 further comprising switch means, disposed in an operative relationship with said wedge for reversing a functional role of the foot activated switch levers in response to the wedge being flipped between the first and second positions.

18. A footpedal comprising:

a frame having a heel portion and a toe portion, the heel and toe portions being disposed at an angle with one another;

a wedge having a generally triangular cross section with first and second sides subtending a front of said wedge;

hinge means, pivotally mounting said wedge to said frame, for enabling said wedge to be flipped between a first position, having the wedge first side generally aligned with the frame heel portion and extending therefrom, and a second position, having the wedge second side generally aligned with the frame toe portion and extending therefrom;

means, defining corrugations in said frame and wedge, for enabling the frame heel portion and wedge first side to assume a first planar relationship in the wedge first position and for enabling the frame toe portion and wedge second side to assume a second planar relationship in the wedge second position, said corrugations being aligned with a longitudinal axis of the footpedal;

means, defining finger holes in the front of said wedge, for enabling manual flipping of the wedge between the front and second positions;

two foot activated switch levers; and means disposing one of the foot activated switch levers on each side of said pedal for enabling activation of the foot activated switch levers by lateral displacement of user's foot.

19. The footpedal according to claim 18 further comprising switch means, disposed in an operative relationship with said wedge, for reversing a functional role of the foot activated switch levers in response to the wedge being flipped between the first and second positions.

* * * * *